(12) United States Patent
Farmer et al.

(10) Patent No.: US 11,286,456 B2
(45) Date of Patent: Mar. 29, 2022

(54) LARGE SCALE PRODUCTION OF LIQUID AND SOLID TRICHODERMA PRODUCTS

(71) Applicant: Locus Agriculture IP Company, LLC, Solon, OH (US)

(72) Inventors: Sean Farmer, North Miami Beach, FL (US); Ken Alibek, Solon, OH (US); Sharmistha Mazumder, Copley, OH (US)

(73) Assignee: LOCUS AGRICULTURE IP COMPANY, LLC, Solon, OH (US)

( * ) Notice: Subject to any disclaimer, the term of this patent is extended or adjusted under 35 U.S.C. 154(b) by 151 days.

(21) Appl. No.: 16/643,535

(22) PCT Filed: Sep. 25, 2018

(86) PCT No.: PCT/US2018/052516
§ 371 (c)(1),
(2) Date: Feb. 29, 2020

(87) PCT Pub. No.: WO2019/067379
PCT Pub. Date: Apr. 4, 2019

(65) Prior Publication Data
US 2020/0224149 A1 Jul. 16, 2020

Related U.S. Application Data

(60) Provisional application No. 62/564,683, filed on Sep. 28, 2017.

(51) Int. Cl.
*C12N 1/04* (2006.01)
*C12N 11/00* (2006.01)
*C12N 1/14* (2006.01)
*C12R 1/885* (2006.01)

(52) U.S. Cl.
CPC ............... *C12N 1/04* (2013.01); *C12N 1/14* (2013.01); *C12N 1/145* (2021.05); *C12R 2001/885* (2021.05)

(58) Field of Classification Search
CPC .......... C12N 1/145; C12N 11/04; C12N 1/04; C12N 1/14; C12R 2001/885; A01N 63/38
See application file for complete search history.

(56) References Cited

U.S. PATENT DOCUMENTS

| | | |
|---|---|---|
| 4,803,800 A | 2/1989 | Romaine et al. |
| 5,296,369 A | 3/1994 | Mortensen et al. |
| 6,263,811 B1 | 7/2001 | Hamdy |
| 7,422,737 B1 | 9/2008 | Nussinovitch et al. |
| 2005/0266036 A1 | 12/2005 | Awada et al. |
| 2008/0107689 A1 | 5/2008 | Seiskari |
| 2008/0318777 A1 | 12/2008 | Lin et al. |
| 2009/0280212 A1 | 11/2009 | Sugimoto et al. |
| 2013/0337108 A1 | 12/2013 | Van Hee |
| 2014/0201870 A1 | 7/2014 | Harman |
| 2015/0044356 A1 | 2/2015 | Bootsma et al. |
| 2016/0083684 A1 | 3/2016 | Li et al. |
| 2016/0152525 A1 | 6/2016 | Chelle et al. |
| 2017/0223956 A1 | 8/2017 | Habib et al. |
| 2018/0098483 A1 | 4/2018 | Fabbri et al. |

FOREIGN PATENT DOCUMENTS

| | | |
|---|---|---|
| CN | 102613252 A | 8/2012 |
| EP | 0544039 A1 | 6/1993 |
| EP | 2390345 A1 | 11/2011 |
| WO | 810338 A1 | 11/1981 |
| WO | 9525163 A1 | 9/1995 |
| WO | 9716974 A1 | 5/1997 |
| WO | 2017035101 A1 | 3/2017 |

OTHER PUBLICATIONS

Vinale F. et al., "Harzianic Acid, an Antifungal and Plant Growth Promoting Metabolite from Trichoderma harzianum", J. Nat. Prod., 2009, vol. 72, pp. 2032-2035. (Year: 2009).*
Zhihui Bai et al. (2011)—CN102613252A—"Method for producing Trichoderma sp. biological control agent from potato starch waste water and mushroom residues", An English machine translation provided by USPTO (Total pp. 1-9). (Year: 2011).*
Duarte, J.C., et al., "Effect of immobilized cells in calcium alginate beads in alcoholic fermentation." AMB Express, 2013, 3(31): 1-8.
Buysens, C. ,et al., "Inoculation of Medicago sativa cover crop with Rhizophagus irregularis and Trichoderma harzianum increases the yield of subsequently-grown potato under low nutrient conditions." Applied Soil Ecology, 2016, 105: 137-143.
El-Katatny, M.H., et al., "Improvement of Cell Wall Degrading Enzymes Production by Alginate Encapsulated *Trichoderma* spp." Food Technol. Biotechnol., 2003, 41(3): 219-225.
Kar, S., et al., "Production of xylanase by immobilized Trichoderma reesei SAF3 in Ca-alginate beads." J. Ind. Microbiol. Biotechnol., 2008, 35: 245-249.

* cited by examiner

*Primary Examiner* — Satyendra K Singh
(74) *Attorney, Agent, or Firm* — Saliwanchik, Lloyd & Eisenschenk

(57) ABSTRACT

The subject invention provides method of producing *Trichoderma* fungi on an industrial scale. In specific embodiments, the subject invention provides methods of producing both a liquid *Trichoderma*-based product and a solid-state *Trichoderma*-based product from the same starting seed culture and inoculant.

19 Claims, No Drawings

LARGE SCALE PRODUCTION OF LIQUID AND SOLID TRICHODERMA PRODUCTS

CROSS-REFERENCE TO A RELATED APPLICATION

This application is a National Stage Application of International Application No. PCT/US2018/052516, filed Sep. 25, 2018; which claims the benefit of U.S. provisional application Ser. No. 62/564,683, filed Sep. 28, 2017, which are incorporated herein by reference in their entirety.

BACKGROUND OF THE INVENTION

Soil-borne pathogenic fungi can cause extensive damage to crops. These parasites cause, for example, damping-off, root-rot, crown-rot, and neck-rot in a wide variety of host plants. The most common pathogenic fungi of this sort are the *Rhizoctonia, Pythium, Fusarium, Phytophotora, Sclerotia, Cercospora, Ralstonia, Fragaria, Rhizopus, Botrytis, Colletotrichum, Magnaporthe* species, and a number of others. *Rhizoctonia, Pythium* and *Sclerotia* species have extraordinarily wide host ranges and are capable of attacking many common commercial crops, such as beans, tomatoes, cotton, peanuts, potatoes, lettuce, and ornamental flowering plants.

The most common methods of controlling these pathogenic fungal species involve application of chemical control agents; however, these chemicals can be expensive, and may be harmful to public health and the environment. Additionally, they can upset the microenvironment of the plants by, for example, altering the surrounding ecosystem.

One alternative to the use of chemicals is the use of biological control agents, which are found naturally in the ecosystem. For example, certain species of *Trichoderma* fungi possess antagonistic properties towards various pests. A number of these fungi are useful when added to soil, where they can multiply and grow in close association with plants' roots. They are capable of partially protecting the roots from invasion by other plant pathogenic fungi and other microbial and animal pests, in addition to helping stimulate plant growth.

The *Trichoderma* can establish strong and long-lasting colonization of root surfaces, penetrating into the epidermis and shallow subsurface cells. These root-microorganism associations cause substantial changes to the plant proteome and metabolism. They produce and/or release a variety of compounds that induce localized or systemic resistance responses, causing a lack of pathogenicity to plants.

Additionally, plants are protected from numerous classes of plant pathogen by responses that are similar to systemic acquired resistance and rhizobacteria-induced systemic resistance. *Trichoderma* spp. can effectively reduce diseases caused by some soil-borne plant pathogens. For example, the species *Trichoderma harzianum, Trichoderma hamatum*, and *Trichoderma viride* have fungicidal activity against *Sclerotium* spp, *Rhizoctonia, Solani, Pythium* spp, *Fusarium* spp, *Cercospora* spp, *Ralstonia* spp, *Fragaria* spp, *Rhizopus* spp, *Botrytis* spp, *Colletotrichum* spp, *Magnaporthe* spp. and many others. Moreover, some strains of *Trichoderma* are able to effectively suppress the growth of some viral and bacterial plant and soil pathogens, as well as produce some significant nematicidal effects.

In addition to protecting plants from pathogens and pests, root colonization by *Trichoderma* spp. frequently enhances root growth and development, crop productivity, resistance to abiotic stresses, and bioavailability of nutrients.

Despite the potential for *Trichoderma* strains to be effective for use in enhancing plant health, the lack of a highly effective large scale production technology for these organisms creates certain obstacles to commercialization. The most common method for growing *Trichoderma* is on traditional solid media, and current methods are too expensive and impractical for commercial adaptation. On the other hand, methods for growing *Trichoderma* in liquid media, i.e., submerged culture, are laboratory or small-scale processes and do not produce *Trichoderma* in the amounts required to make them commercially viable (e.g., for treatments of hundreds, thousands, or even millions of acres of crops).

Propagation of *Trichoderma* by a large scale submerged culture process, or a combination of both submerged and solid state, would be most suitable for commercial production; however such commercial processes are not known on a large-scale and at a low cost. Thus, there is a need for improved methods of producing *Trichoderma* fungi that can be scaled for commercial use.

BRIEF SUMMARY OF THE INVENTION

This invention relates to the large-scale production of both liquid and dry microbe-based products for commercial application. Specifically, materials and methods are provided for efficient cultivation of fungi, such as *Trichoderma*, and/or their growth by-products on a large scale. Methods are also provided for using these microbe-based products. Advantageously, the subject invention can be used as a "green" process for producing microorganisms on a large scale and at low cost, without releasing harmful chemicals into the environment.

The subject invention provides systems for the efficient production and use of beneficial microbes, as well as for the production and use of substances, such as metabolites, derived from these microbes and the fermentation medium in which they are produced. Organisms according to the subject invention include, for example, yeasts, fungi, bacteria, archaea, and plant cells. In preferred embodiments, the microorganisms are fungi. Even more preferably, the microorganisms are *Trichoderma* fungi, including, but not limited to, *Trichoderma harzianum, Trichoderma viride*, and/or *Trichoderma hamatum*.

In specific embodiments, the subject invention provides microbe-based compositions comprising *Trichoderma* clade fungi and/or their growth by-products. The *Trichoderma*-based products can be, for example, in liquid or dry form. Advantageously, in one embodiment, the microbe-based products can be in the form of an inoculant, which can be scaled up to industrial scale concentrations for commercial applications using submerged fermentation, solid-state fermentation, and/or combinations or hybrids thereof.

The *Trichoderma*-based products can comprise the microorganisms themselves and/or their growth by-products. The microorganisms can be viable, active or in an inactive form. They can be in the form of vegetative cells, spores, conidia, mycelia, hyphae and/or a combination thereof. Optionally, the compositions can comprise the fermentation medium in which the microorganisms were produced, as well as residual and/or added nutrients for microbial growth.

Furthermore, the subject *Trichoderma*-based products can be formulated as, for example, biofertilizers and/or biopesticides, which can be useful in applications including, for example, gardening, horticulture, greenhouse production, as well as for large-scale farming and reforestation operations. The product can also be useful, e.g., as seed treatments, for soil reclamation, for enhanced production, for enhanced plant root health, and/or for plant growth stimulation.

In preferred embodiments, the subject invention provides for cultivation of both liquid form microbe-based products and solid-state microbe-based products from one seed culture. In specific embodiments, the microbe-based products are a *Trichoderma*-based product according to the subject description.

The methods of producing microorganisms can comprise either submerged or solid-state fermentation, or hybrids and/or combinations thereof. In one embodiment, the methods can be used to produce inocula for the production of microbe-based products on an industrial scale.

In certain embodiments, the subject invention provides methods of producing both liquid and solid-state microbe-based products (e.g., *Trichoderma*-based products) from one seed culture in industrial scale amounts, the methods comprising:

(a) preparing an alginate-agar bead inoculant from a *Trichoderma* seed culture;

(b) cultivating the alginate-agar bead inoculant in liquid nutrient culture medium in a reactor to produce a desired microbial density in the bead;

(c) harvesting the alginate-agar bead inoculant from the liquid culture medium;

(d) preparing the liquid form *Trichoderma*-based product, wherein the cultivated alginate-agar bead inoculants are used to inoculate a submerged fermentation reactor, and/or preparing the solid-state *Trichoderma*-based product, wherein the cultivated alginate-agar bead inoculants are used to inoculate a solid-state fermentation reactor.

More specifically, in one embodiment, the methods comprise (a), preparing a *Trichoderma* inoculant in the form of alginate beads comprising a pre-made seed culture, nutrient components, sodium alginate and agar. The alginate bead inoculant can be prepared by combining sterile liquid nutrient medium with a sterile mixture of 1% agar and 2% sodium alginate and a 5% homogenous seed culture slurry to produce an inoculum solution.

A dripping showering device and a peristaltic pump are then used to drip the inoculum solution into a mixing vessel having a 1% solution of calcium chloride therein. During the dripping process, the droplets of inoculum form gel beads comprising nutrient components and *Trichoderma* culture embedded in alginate-agar mass. After forming the beads, residual liquid in the mixing vessel can be released and disposed of into a liquid waste system.

In one embodiment, the methods comprise (b), cultivating the alginate-agar bead inoculant in liquid nutrient culture medium to a desired microbial density in and/or on the beads. In certain embodiments, the alginate-agar bead inoculants are collected from the mixing vessel and then cultivated in a reactor containing a sufficient volume of a suitable liquid nutrient medium to permit a high concentration of *Trichoderma* mycelia to disperse inside and throughout the surface of each alginate-agar bead. In certain embodiments, some *Trichoderma* is also produced into the liquid nutrient medium from the beads.

In one exemplary embodiment, the seed culture for producing the inoculant beads can be obtained from a culture produced using submerged fermentation in a suitable liquid culture medium and under continuous aeration and agitation. Temperature and pH are maintained at constant, or essentially constant levels throughout this step (i.e., temperature within about 28° C. to about 30° C.; pH within about 5.0 to about 6.5). The seed culture can be grown for any time period sufficient to achieve a desired concentration and/or density of the microorganism, and the homogenized to produce a seed culture slurry.

In one embodiment, the method comprises (c), harvesting the alginate-agar bead inoculants from the liquid culture medium after the desired mycelial density is achieved. These inoculant beads can comprise a high concentration of *Trichoderma* inside and on the surface. The beads can be utilized to seed scaled-up cultures immediately after harvesting, or the beads can be processed for short- and/or long-term storage.

In certain embodiments, the method further comprises, after step (c) and before step (d), processing the beads for storage. This can comprise placing the harvested alginate-agar bead inoculants into a cryopreservation solution so that the inoculants can be stored in a freezer or a refrigerator without loss of microbe viability. Preferably, the cryopreservation solution comprises water and glycerol, at a ratio of, for example, 50%. This solution, with the bead inoculants placed therein, can be stored for extended periods of time at temperatures of, for example, −80° C. to −10° C., or for shorter time periods in a standard refrigerator, at, for example, −10° C. to 4.0° C., without compromising the efficacy of the inoculant culture. In certain embodiments, the beads are stored in groups of, for example, 1-50 beads in sealed flasks.

In one embodiment, the methods further comprise (d), preparing a scaled-up liquid form *Trichoderma*-based product and/or preparing a scaled-up dry, or solid, form *Trichoderma*-based product. In certain embodiments, (d) comprises using the inoculant beads to seed a scaled-up culture in either a submerged fermentation reactor, a solid-state fermentation reactor, or in a hybrid or modified form thereof, depending upon whether a liquid or solid product is desired.

In certain embodiments, preparation of a liquid form product comprises seeding a submerged fermentation reactor having liquid nutrient medium therein with an alginate-agar inoculant bead of the subject invention.

In a specific embodiment, the inoculant beads are added to a liquid nutrient medium in, for example, a 200-250 gallon (working volume) reactor under substantially constant mixing and aeration at a temperature from about 28° C. to about 30° C. The pH of the medium is maintained throughout the fermentation process from about 5.0 to about 6.5. The culture is maintained for 3-10 days or until the density of conidia produced from the inoculant is not less than $5 \times 10^8$ conidia per ml of liquid medium.

In some embodiments, preparation of a liquid form product can comprise simply cultivating any residual microorganisms that remain in the liquid medium of step (b) after the inoculant beads have been harvested according to step (c). The residual microorganisms can be cultivated in a second reactor or in the same reactor where step (b) occurred.

In one embodiment, preparation of the liquid microbe-based product further comprises increasing the concentration of microorganism up to 1 billion propagules per milliliter, and adding further additives, preservatives and/or pH adjusters as needed. The "readymade" liquid product can then be filled into containers (e.g., 1 gallon containers), hermetically sealed and labeled for a variety of uses, including in commercial settings.

In certain embodiments, the method comprises preparing a scaled-up solid state *Trichoderma*-based product using solid-state fermentation or a hybrid or modification thereof. The alginate-agar bead inoculants can be mixed with a solid or semi-solid substrate, such as vermiculate or foodstuffs (e.g., corn flour, rice, pasta or beans). The substrate is preferably moistened in an appropriate nutrient medium, and then the mixture can be cultivated for about 3 to about 10 days or more, or from 5 to about 6 days, in an incubator. The substrate and culture can then be blended and/or milled and dried to prepare a *Trichoderma*-based product in powder form for a variety of uses, including in commercial settings.

In some embodiments, the subject invention also provides methods of producing a metabolite and/or growth by-product of a fungi, wherein the method comprises cultivating the fungi under conditions favorable for growth and metabolite and/or growth by-product production, and optionally, purifying the metabolite and/or growth by-product. In specific embodiments, the metabolite and/or growth by-product is an enzyme, biopolymer, acid, solvent, biosurfactant, amino acid, nucleic acid, peptide, protein, lipid and/or carbohydrate.

DETAILED DESCRIPTION OF THE INVENTION

This invention relates to the large-scale production of both liquid and dry microbe-based products for commercial application. Specifically, materials and methods are provided for efficient cultivation of fungi, such as *Trichoderma*, and/or their growth by-products on a large scale. Methods are also provided for using these microbe-based products.

The subject invention provides systems for the efficient production and use of beneficial microbes, as well as for the production and use of substances, such as metabolites, derived from these microbes and the fermentation medium in which they are produced. Organisms according to the subject invention include, for example, yeasts, fungi, bacteria, archaea, and plant cells. In preferred embodiments, the microorganisms are fungi. Even more preferably, the microorganisms are *Trichoderma* fungi, including, but not limited to, *Trichoderma harzianum*, *Trichoderma viride*, and/or *Trichoderma hamatum*.

In specific embodiments, materials and methods are provided for cultivating liquid and solid-state microbe-based products comprising *Trichoderma* clade fungi, and/or *Trichoderma* growth by-products, using submerged fermentation, solid-state fermentation, or hybrids and/or combinations thereof. In one embodiment, the methods can be used to produce inocula for the production of these microbe-based products on an industrial scale.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of microbial propagule, or a mixture of these. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells may be totally absent, or present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$ or more cells or propagules per milliliter of the composition. As used herein, a propagule is any portion of a microorganism from which a new and/or mature organism can develop, including but not limited to, cells, mycelia, hyphae, cysts, spores (e.g., reproductive spores, conidia, endospores and/or exospores), buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, the terms "inoculum" or "inoculant" (plural "inocula") can be encompassed within the term "microbe-based product." As used herein, inoculum means a microbe-based product that can be used, for example, as a seed culture to inoculate a larger scale fermentation system or process. The inoculum can be scaled in such a fermentation system to produce desired quantities of microbe-based compositions and products.

As used herein, an "isolated" or "purified" nucleic acid molecule, polynucleotide, polypeptide, protein, organic compound such as a small molecule (e.g., those described below), or other compound is substantially free of other compounds, such as cellular material, with which it is associated in nature. For example, a purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

As used herein, the phrases "scaled-up," "large-scale," "commercial scale," and "industrial scale," can be used interchangeably, and refer to products that, by their volume, concentration, amount, contents, and/or potency, are capable of being used in industrial and/or commercial applications. For example, an industrial scale amount of a liquid microbe-based product or a dry microbe-based product dissolved in a liquid carrier, can comprise from 100 gallons to 10,000 gallons or more. Industrial and/or commercial applications can include, e.g., gardening, horticulture, greenhouse production, agriculture, soil reclamation, bioremediation, reforestation, and pest suppression.

As used herein, "harvested" refers to removing some or all of the microbe-based composition from a growth vessel.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Methods of Producing *Trichoderma*-Based Products

The subject invention provides methods for cultivation of *Trichoderma* microorganisms and production of microbial metabolites and/or other by-products of microbial growth. In some embodiments, methods are provided for producing both dry and liquid form *Trichoderma*-based products. The methods of producing microorganisms can comprise either submerged culture, solid state fermentation, or hybrids and/or combinations thereof. As used herein "fermentation" refers to cultivation and/or growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel (e.g., reactor) used according to the subject invention may have functional controls/sensors or may be connected to functional controls/sensors to measure important factors in the cultivation process, such as pH, oxygen, pressure, temperature, humidity, viscosity and/or microbial density and/or metabolite concentration.

The reactor vessel may be inoculated with a microorganism of choice. Preferably, the vessel is inoculated with an inoculant as produced according to the subject invention, e.g., an alginate-agar inoculant bead as described herein. Depending upon the size of the vessel, the number of inoculants needed to inoculate a vessel for scaled-up production can range from 1 inoculant bead to 40 or 50 beads, or more.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

The method can provide oxygenation to the growing culture. One embodiment utilizes slow motion of air to remove low-oxygen containing air and introduce oxygenated air. In the case of submerged fermentation, oxygenated air may be ambient air supplemented daily through mechanisms including impellers for mechanical agitation of the liquid, and air spargers for supplying bubbles of gas to the liquid for dissolution of oxygen into the liquid.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can further comprise supplementing the cultivation with a carbon source. The carbon source is typically a carbohydrate, such as glucose, sucrose, lactose, fructose, trehalose, mannose, mannitol, maltose, potato dextrose, cellulose, starch and/or laminarin; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, canola oil, vegetable oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process to protect the culture against contamination from undesirable microorganisms. Additionally, antifoaming agents may also be added to prevent the formation and/or accumulation of foam when gas is produced during cultivation.

The pH of the mixture should be suitable for growth of fungi, particularly of *Trichoderma*. In certain embodiments, the pH is about 5.0 to about 7.0, preferably about 5.0 to about 6.5. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of *Trichoderma* microorganisms and production of the microbial by-products can be performed in a batch, quasi-continuous, or continuous processes.

In one embodiment, the method for cultivation is carried out at about 5° C. to about 100° C., preferably, 15° C. to 60° C., more preferably, 25° C. to 30° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and pH may be exploited to control bacterial growth.

In one embodiment, the subject invention further provides a method for producing microbial metabolites such as ethanol, lactic acid, beta-glucan, proteins, peptides, metabolic intermediates, polyunsaturated fatty acid, and lipids, wherein the method comprises cultivating a microorganism under conditions favorable for growth and metabolite expression. In specific embodiments, the metabolite is an enzyme, biopolymer, acid, solvent, biosurfactant, amino acid, nucleic acid, peptide, protein, lipid and/or carbohydrate. The metabolite content produced by the method can be, for example, at least 20%, 30%, 40%, 50%, 60%, 70%, 80%, or 90%.

In the case of submerged fermentation, the biomass content of the fermentation broth may be, for example from 5 g/l to 180 g/l or more. In one embodiment, the solids content of the broth is from 10 g/l to 150 g/l.

The microbial growth by-product produced by *Trichoderma* may be retained in the microorganisms or secreted into the growth medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the medium). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or substrate, or can contain cells. In this manner, a quasi-continuous system is created.

Advantageously, the method does not require complicated equipment or high energy consumption. The *Trichoderma* can be cultivated at small or large scale on site and utilized, even being still-mixed with their media. Similarly, the microbial metabolites can also be produced at large quantities at the site of need.

Organisms that can be cultured using the subject invention can include, for example, yeasts, fungi, bacteria, archaea, and plant cells. In preferred embodiments, the microorganisms are fungi. Even more preferably, the microorganisms are *Trichoderma* fungi, including, but not limited to, *Trichoderma reesei, Trichoderma harzianum* (*Trichoderma narcissi*), *Trichoderma viride*, and/or *Trichoderma hamatum*.

Other fungi can also be produced according to the subject invention, including Mycorrhizae, ectomycorrhizal fungi, yeasts, such as *Starmerella bombicola*, and even spores of mushroom-forming fungi, such as shiitake (*Lentinula edodes*).

According to the subject invention, it is possible to grow large-scale, commercial quantities of *Trichoderma*-based products. Advantageously, *Trichoderma* can be grown within 3 to 10 days, or 5 to 6 days, to yields of $5 \times 10^8$ to $5 \times 10^9$ conidia per ml of liquid culture using a 200 gallon fermentation reactor; and to yields of more than $1 \times 10^9$ conidia per gram of dry product in an incubator, such as a proofing oven-type reactor.

In certain embodiments, the subject invention provides methods of producing both liquid and solid-state microbe-based products (e.g., *Trichoderma*-based products) from one seed culture in industrial scale amounts. Advantageously, the use of alginate-agar bead inoculants (or "inoculant beads," "bead inoculants," "beads," or "inoculants") according to the subject invention allows for the inoculation of a reactor with a much higher cell concentration than could be achieved if a standard liquid inoculant was used. A "high concentration" refers to, for example, at least $10^1$, $10^2$, $10^3$, $10^4$, $10^5$, $10^6$, $10^7$, $10^8$, $10^9$, $10^{10}$, $10^{11}$, $10^{12}$, $10^{13}$ or more cells or propagules of a desired microorganism per unit (weight or volume).

In preferred embodiments, the methods comprise:

(a) preparing an alginate-agar bead inoculant from a *Trichoderma* seed culture;

(b) cultivating the alginate-agar bead inoculant in liquid nutrient culture medium in a reactor to produce a desired microbial density in the bead;

(c) harvesting the alginate-agar bead inoculant from the liquid culture medium;

(d) preparing the liquid form *Trichoderma*-based product, wherein the cultivated alginate-agar bead inoculants are used to inoculate a submerged fermentation reactor, and/or preparing the solid-state *Trichoderma*-based product, wherein the cultivated alginate-agar bead inoculants are used to inoculate a solid-state fermentation reactor.

More specifically, in one embodiment, the methods comprise (a), preparing a *Trichoderma* inoculant in the form of alginate-agar beads comprising a pre-made seed culture, nutrient components, sodium alginate and agar. The seed culture (e.g., a 5% homogenous seed culture slurry) can be dissolved in sterile nutrient medium, and combined with a mixture of agar and sodium alginate to produce an inoculum solution.

The concentration of the alginate in the inoculum solution can be about 0.1 to about 3.0%, preferably about 0.5 to about 2.5%, more preferably about 2.0%. The concentration of the agar can be about 0.1% to about 2.0%, preferably about 0.5% to about 1.5%, more preferably about 1.0%. In one embodiment, the alginate-agar can be autoclaved and/or heated prior to mixing with the seed culture.

A dripping showering device and a peristaltic pump are then used to drip the inoculum solution into a mixing vessel having a calcium chloride solution therein. During the dripping process, the droplets of inoculum form gel beads comprising nutrient components and *Trichoderma* fungal particles embedded in alginate-agar mass. In certain embodiments, about 5 to 10 kg of alginate bead inoculant is produced from one batch. After forming the beads, residual liquid in the mixing vessel can be released and disposed of into a liquid waste system.

In certain embodiments, the $CaCl_2$ solution can be about a 1.0% to about a 5.0% solution, preferably about a 1% to 2% solution.

In one embodiment, the mixing vessel is a mobile rotating tank equipped with a motor. The tank can be about 2 to about 4, to about 6 cubic feet in volume, or more, and made of polyethylene, any other polymeric source, or metal. The rotating tank can contain, for example, 5 to 10 gallons of a 1% solution of calcium chloride.

In one exemplary embodiment, the seed culture for producing the inoculant beads can be obtained from a culture produced using submerged fermentation in a suitable liquid culture medium (see, e.g., Elad et al. (1982), incorporated by reference herein) and under continuous aeration and agitation. Temperature and pH are maintained at constant, or essentially constant levels throughout this step (i.e., temperature within about 28° C. to about 30° C.; pH within about 5.0 to about 6.5). The seed culture can be grown for any time period sufficient to achieve a desired concentration and/or density of the microorganism, and the homogenized to produce a seed culture slurry.

In one embodiment, the methods comprise (b), cultivating the alginate-agar bead inoculant in liquid nutrient culture medium to a desired microbial density in and/or on the beads. In certain embodiments, the alginate-agar bead inoculants are collected from the mixing vessel and then cultivated in a reactor containing a suitable liquid nutrient medium to permit a high concentration of *Trichoderma* mycelia to grow inside each alginate-agar bead and disperse over the surface of each bead. In certain embodiments, the cultivation parameters for step (b), such as temperature, medium, and pH, can be the same as what is used for producing the initial seed culture. In certain embodiments, a certain amount of *Trichoderma* cells also grow in the liquid nutrient medium, unattached from the inoculant beads.

In one embodiment, the method comprises (c), wherein alginate-agar inoculant beads comprising a high concentration of *Trichoderma* are harvested from the liquid medium. These inoculant beads can comprise a high concentration of *Trichoderma* inside and/or on the surface. The beads can be utilized to seed scaled-up cultures immediately after harvesting, or the beads can be processed for short- and/or long-term storage. In some embodiments, the beads are placed into a container, such as a tube or a flask, upon harvesting.

In certain embodiments, the method can further comprise, after step (c) and before step (d), processing the beads for storage. This can comprise suspending the harvested alginate-agar bead inoculants in a cryopreservation solution so that the inoculants can be stored in a freezer or a refrigerator without loss of microbe viability. Preferably, storage occurs in a tube, flask, cylinder, vial or dish, or other similar standard laboratory container.

In certain embodiments, the cryopreservation solution comprises water and a cryoprotectant substance. Cryoprotectants are well-known antifreeze compounds that are capable of protecting cells and other biological tissue from damage due to freezing and ice formation. Many animal and plant species native to colder climate zones produce natural cryoprotectants to protect their bodies and cells. Isolated and synthetic cryoprotectants are also used in preservation of living materials for biological research and in food products.

Exemplary cryoprotectants useful according to the present invention include, but are not limited to, glycols such as ethylene glycol, propylene glycol, and glycerol, dimethyl sulfoxide (DMSO), trehalose, 2-Methyl-2,4-pentanediol (MPD), and sucrose.

In preferred embodiments, the cryopreservation solution comprises water and glycerol, where the percentage of glycerol is from 35% to 75%, preferably about 50%.

This solution, with the bead inoculants placed therein, can be stored for extended periods of time in a freezer set to, for example, about −80° C. to about 0° C., preferably from about −80° C. to about −20° C. Storage at these temperatures can last as long as needed while retaining the efficacy and viability of the biological material within, for example, as long as 1 month, 6 months, or 1, 2, 3, 4, 5, or even 10 or more years.

In certain embodiments, when shorter term storage is desired, for example, 1 month or less, the containers having inoculant beads suspended in glycerol solution can be stored in a refrigerator set to a temperature of about −15° C. to about 4° C., or about −10° C. to about 4° C., or about 0° C. to 4° C.

In certain embodiments, the beads are stored in groups comprising the cryopreservation solution and, for example, 1-50 beads per one sealed container.

In other embodiments, the beads are not harvested from the fermentation reactor according to (c), but instead, the cryopreservation solution is poured directly into the fermentation reactor used in step (b) and the reactor itself is used to store and preserve the entire batch of beads. The temperature inside the reactor can be adjusted accordingly.

In one embodiment, the methods further comprise (d), preparing a scaled-up liquid form *Trichoderma*-based product and/or preparing a scaled-up dry, or solid, form *Trichoderma*-based product. In certain embodiments, (d) comprises using the inoculant beads to seed a scaled-up culture in either a submerged fermentation reactor, a solid-state fermentation reactor, or in a hybrid or modified form thereof, depending upon whether a liquid or solid product is desired.

In certain embodiments, preparation of a liquid form product comprises seeding a submerged fermentation reactor having liquid nutrient medium therein with an alginate-agar inoculant bead of the subject invention. In some embodiments, when, for example, the inoculant beads have been preserved using the glycerol solution, the beads can be taken directly from the freezer or refrigerator where they were being stored and used to seed the reactor. Advantageously, the subject methods allow for inoculating multiple large-scale fermentation reactors (e.g., having from a 100 to 2,000-gallon, to 10,000-gallon volume or more) from a single seed culture.

In a preferred embodiment, the large-scale (scaled-up) production is carried out in a novel, portable and distributable reactor. Fermentation using this system is conducted as a batch process, without agitation, but with mixing and aeration. In one embodiment, the system comprises one high volume tank. The reactor can further comprise a mixing system comprising a first and a second tubing system, where the first tubing system is located on the left vertical side of the tank and the second is located on the right vertical side of the tank. Each tubing system has a connection at the bottom of the tank and at the top of the tank. Each tubing system can be equipped with pumps capable of transferring culture liquid from the bottom of the tank, through the tubing, and back into the top of the tank at a speed of up to about 200 gallons per minute. These tubing systems can operate continuously throughout the fermentation process to mix the culture.

This single-tank reactor can comprise a sparger supplied with filtered air by an air blower capable of providing 2 liters of air per liter of culture per minute. The filtered air for sparging can be generated via a high volume aquatic pumping system, comprising pumps supplied with additional filters.

The system reactor preferably has a working volume of 200 to 2,000 gallons but can be smaller (e.g., 100-200 gallons) or greater (e.g., up to 10,000 gallons or more). However, sizes and configuration of reactors may vary (depending on, for example, final volume of industrial scale microbe-based product that is desired). The system can be used for microbial cultures of a variety of strains and species, and with practically no limit to the total amount of microbe-based product that can be produced.

In some embodiments, to reduce the cost of culture production and ensure scalability of production, the fermentation systems are not sterilized using traditional methods. Instead, a method of empty vessel sanitation is used, which comprises treating internal surfaces with 2-3% hydrogen peroxide and rinsing with bleach and high pressure hot water. Additionally, in order to reduce the probability of significant contamination, water used for preparing the cultivation culture is filtered through 0.1-micrometer filter. Culture medium components are temperature decontaminated at 85-90° C., or dissolved in 3% hydrogen peroxide (dry components and $H_2O$ ratio is 1:3 v/v).

In certain embodiments, the medium for use in the step of scaled-up production of *Trichoderma* is a liquid basal nutrient medium comprising potato dextrose broth or glucose as a carbon source. The medium could also comprise an additional carbon source and a nitrogen source. The additional carbon source can be selected from glucose, sucrose, maltose, fructose, cellulose, starch and laminarin. The medium can also optionally comprise malt extract.

A variety of nitrogen sources can be used in the liquid basal nutrient medium, though preferably nitrates or nitrites are used. In preferred embodiments, ammonium nitrate is used as a nitrogen source.

The liquid basal nutrient medium can also comprise suitable amounts of minerals and trace elements, such as $MgSO_4$, $FeCl_2$, $MnSO_4$, $ZnSO_4$, $KCl$, and $K_2HPO_4$. Other trace elements and minerals may also be added.

In some embodiments, the liquid basal nutrient medium comprises yeast extract as a vitamin source. In order to develop an "organic" product, antibacterial compounds, such as antibiotics, should not be included in the nutrient medium. Instead, natural compounds with antibacterial properties should be utilized (e.g., biosurfactants such as sophorolipids and rhamnolipids; and/or hop acids or hops), provided that they do not have an adverse effect on the microorganism being produced by the subject methods (e.g., *Trichoderma* species).

In an exemplary embodiment, the liquid basal nutrient medium for large-scale production of *Trichoderma* in the subject reactor systems comprises the components in the amounts listed in Table 1 of Example 1 below.

The fermentation temperature for large-scale production of *Trichoderma*-based products should range between about 25 to about 32° C., preferably between about 28 and 30° C. pH should range between about 5.0 to about 6.5, preferably between about 5.5 to about 6.0. pH stabilization during the fermentation is not critical, but it pH should not fall below 4.5. If necessary, control or maintenance of pH in the course of the fermentation may be accomplished using manual or automatic techniques conventional in the art, such as using automatic pH controllers for adding basic components. Preferred bases employed for pH control include but are not limited to NaOH and KOH.

Preferably, the culture is maintained for 3 to 10 days, or more, or 5 to 6 days, until the density of the conidia produced from the alginate inoculant beads is approximately $5 \times 10^8$ to $5 \times 10^9$ conidia per milliliter of liquid culture.

In some embodiments, preparation of a liquid form product can comprise simply cultivating any residual microorganisms that remain in the leftover liquid medium after the inoculant beads have been harvested according to step (c). The residual microorganisms can be cultivated in a second reactor or in the same reactor where step (b) occurred.

In one embodiment, preparation of the liquid microbe-based product further comprises growing the concentration of microorganism up to 1 billion propagules per milliliter, and adding further additives, preservatives and/or pH adjusters as needed. The "readymade" liquid product can then be filled into containers (e.g., 1 gallon containers), hermetically sealed and labeled for a variety of uses, including in commercial settings.

In certain embodiments, the method comprises preparing a scaled-up solid state *Trichoderma*-based product using solid-state fermentation or a hybrid or modification thereof. The alginate-agar bead inoculants can be mixed with a solid or semi-solid substrate, such as vermiculate or foodstuffs (e.g., corn flour, pasta, rice or beans). The substrate is preferably moistened in an appropriate nutrient medium. For example, the trays can be sprayed regularly (e.g., once a day, once every other day, once per week) with a sterile nutrient medium throughout cultivation.

The mixture can be cultivated for about 3 to about 10 days or more, or from 5 to about 6 days, in an incubator. The substrate and culture can then be blended and/or milled and dried to prepare a *Trichoderma*-based product in powder form for a variety of uses, including in commercial settings.

In some embodiments, when, for example, the inoculant beads have been preserved using the glycerol solution, the beads can be taken directly from the freezer or refrigerator where they were being stored and used to seed the solid or semi-solid substrate.

In specific embodiments, producing solid state commercial product of, for example, *Trichoderma*, can comprise mixing the collected beads with the substrate and nutrient medium and incubating the mixture in trays. In certain embodiments, the trays are incubated in proofing ovens or a similar heating apparatus.

In an exemplary embodiment, when vermiculite is used, the vermiculate is heat sterilized at 150° C. overnight in an oven. About 3 to 4 parts of sterilized vermiculite is thoroughly mixed with 1 part alginate-agar beads. The mixture is spread thinly on the trays. Cultivation can then take place for about 5 to about 6 days, to about two weeks, with aeration by ambient air.

After the process of cultivation is finished, the temperature in the incubator be increased to about 40° C., and drying can take place for about 3 to about 4 days using dry air supplementation and vacuuming of moistened air. The dried microbe-based product can be ground, milled or micronized to a desired particle size. The propagule concentration should not be less than $1\times10^9$ conidia per one gram of the dry product, and can reach as high as $1\times10^{10}$, $1\times10^{11}$, $1\times10^{12}$ or even $1\times10^{13}$ propagules per gram.

The dry microbial product can then be mixed with dry diatomaceous earth and commercial compost to redistribute the residual moisture and to standardize the final product. The concentration of propagules after mixing can be, for example, about $1\times10^6$ conidia per gram. This final, dry *Trichoderma*-based product can then be packaged in labeled plastic bags and hermetically sealed for commercial realization.

In certain embodiments, the final dry *Trichoderma*-based product can comprise carbon, protein and/or mineral sources.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a fish farm). For example, the microbe growth facility may be less than 300, 250, 200, 150, 100, 75, 50, 25, 15, 10, 5, 3, or 1 mile from the location of use.

Because the microbe-based product is generated on-site or near the site of application, without the requirement of stabilization, preservation, prolonged storage and extensive transportation processes of conventional production, a much higher density of live microorganisms can be generated, thereby requiring a much smaller volume of the microbe-based product for use in an on-site application. This allows for a scaled-down bioreactor (e.g., smaller fermentation tank; smaller supplies of starter material, nutrients, pH control agents, and de-foaming agent, etc.), which makes the system efficient. Furthermore, local production facilitates the portability of the product.

Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have undergone vegetative cell stabilization or have sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells, inactivated cells, or a mixture of vegetative cells, inactivated cells, spores, mycelia and/or other microbial propagules. Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell- and/or propagule-count product and the associated medium and metabolites in which the microbes are originally grown.

Advantageously, in preferred embodiments, the systems of the subject invention harness the power of naturally-occurring local microorganisms and their metabolic by-products to treat plant pathogenic bacteria. Local microbes can be identified based on, for example, salt tolerance, ability to grow at high temperatures, and the use of genetic identification of sequences. Additionally, the microbe growth facilities provide manufacturing versatility by their ability to tailor the microbe-based products to improve synergies with destination geographies.

The cultivation time for the individual vessels may be, for example, from 1 day to 2 weeks or longer. The cultivation product can be harvested in any of a number of different ways.

Local production and delivery within, for example, 24 hours of fermentation results in pure, high microbe density compositions and substantially lower shipping costs. Given the prospects for rapid advancement in the development of more effective and powerful microbial inoculants, consumers will benefit greatly from this ability to rapidly deliver microbe-based products.

The microbe-based products of the subject invention can be used in a variety of unique settings because of, for example, the ability to efficiently deliver: 1) fresh fermentation broth with active metabolites; 2) a mixture of microbes and fermentation broth; 3) a composition with live cells, or spores, mycelia, conidia or other microbial propagules; 4) compositions with a high density of microbes, including live cells and/or spores, mycelia, conidia or other microbial propagules; 5) microbe-based products on short-order; and 6) microbe-based products in remote locations.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Production of Seed Culture and Propagule Count Method

Seed culture of *Trichoderma* was prepared at a pH of 5.5 with the medium composition of Table 1.

TABLE 1

Medium composition for *Trichoderma* production

| Component | Quantity (g/L) |
|---|---|
| Glucose | 30 |
| Yeast extract | 2.8 |

TABLE 1-continued Medium composition for Trichoderma production

| Component | Quantity (g/L) |
|---|---|
| Liquid potato extract | 0.5 (ml/L) |
| $NH_4NO_3$ | 1.0 |
| $KH_2PO4$ | 1.0 |
| $MgSO_4 \cdot 7H_2O$ | 0.5 |
| KCl | 0.5 |
| $FeSO_4 \cdot 7H_2O$ | 0.01 |
| $ZnSO_4 \cdot 7H_2O$ | 0.01 |
| $CuSO_4 \cdot 5H_2O$ | 0.005 |

Flasks were inoculated with fungal conidia and actively growing hyphae from a plate. For homogenous seed culture preparation, the mycelial pellets were broken with glass beads. Shake flasks were incubated at 30° C. for 3-4 days at 200 rpm. After 3-4 days Trichoderma formed mycelial pellets for larger scale fermentation. The entire content of the flasks containing fermented substrate and biomass was completely homogenized with glass beads for a predetermined time of 180 seconds to obtain conidia and mycelium fragments. After homogenization, serial dilutions were prepared and the micro propagule counts were estimated.

Example 2—Alginate-Agar Bead Culture Development

Alginate beads containing Trichoderma are prepared by combining the liquid media of Table 1 above with a mixture of 1% agar and 2% sodium alginate. This mixture is combined with 5% homogenous seed culture slurry of Example 1. After mixing well, the entire mixture is dropped slowly into autoclaved 100 mM calcium chloride solution with constant mixing. Alginate beads with fungal particles inside are formed immediately. Alginate beads are then collected from the solution and the remaining liquid is discarded.

Example 3—Conidia Production in Liquid Culture

Conidia are harvested from a biologically pure culture of Trichoderma harzianum that is grown in a reactor. The nutrient medium composition comprises: glucose (30 g/L), yeast extract (2.8 g/L), $KH_2PO_4$ (1.0 g/L), $MgSO_4.7H_2O$ (0.5 g/L), KCl (0.5 g/L), $FeSO_4.7H_2O$ (0.01 g/L), $ZnSO_4.7H_2O$ (0.01 g/L), $CuSO_4.5H_2O$ (0.005 g/L). Initial pH of cultivation is 5.5 and temperature is 25-28° C. The amount of culture is about 100 gallons. After cultivation for 5 days, the yield is more than approximately $5 \times 10^8$ to $5 \times 10^9$ conidia per milliliter of liquid culture.

Example 4—Solid State Culture of Trichoderma in Vermiculite Substrate

Vermiculite and diatomaceous earth is heat sterilized at 150° C. overnight in a heating oven. Three to four parts vermiculite is mixed with one part diatomaceous earth and either one part Trichoderma inoculant beads or 150 ml seed culture slurry. The components are mixed with 1 liter of nutrient medium. This mixture is spread thinly on a tray and incubated at 30° C. for 4-6 days in a proofing oven, with aeration by ambient air. Conidia are first observed at day 4.

The yield from one tray is approximately 652.60 grams before drying and processing. After the process of cultivation is finished, the temperature in the incubator can be increased to about 40° C., and drying can take place for about 3 to about 4 days using dry air supplementation and vacuuming of moistened air. After drying and thorough milling, as many as 4 pounds or more of Trichoderma product can be produced per tray. The dried microbe-based product can be ground, milled or micronized to a desired particle size, and then mixed with dry diatomaceous earth and commercial compost to redistribute the residual moisture and to standardize the final product. The propagule concentration should not be less than $1 \times 10^6$ conidia per gram of the dry product, preferably, not less than $1 \times 10^9$.

This final, dry Trichoderma-based product can then be packaged in labeled plastic bags and hermetically sealed for commercial realization. The product can be dissolved in water for a variety of applications.

Example 5—Solid State Fermentation of Fungal Spores in Corn Flour Substrate

For growing fungal spores, such as Trichoderma spp., 250 g of nixtamilized corn flour is mixed with deionized water and sterilized in a stainless steel steam pan, then sealed with a lid and pan bands. These pans with corn flour media are aseptically inoculated with fungal seed culture. The pans are then incubated in a proofing oven at 30° C. for 10 days. After 10 days, approximately $1 \times 10^9$ propagules/g were harvested.

Example 6—Solid State Fermentation of Fungal Spores in Pasta Substrate

For growing Trichoderma spp., 250 grams of dry corn flour pasta mixed with 1000 L of water is spread onto stainless steel steam pans. The steams pans, pasta and water are then autoclaved, and then sealed with sterilized lids and pan bands. The pasta-water substrate is then aseptically inoculated with Trichoderma seed culture. The pans are incubated in the proofing oven at 30° C. for 8 days. After 8 days, approximately $1 \times 10^9$ propagules/g of Trichoderma are harvested.

We claim:

1. A method of producing a liquid form Trichoderma-based product and a solid state Trichoderma-based product, the method comprising the steps:
   (a) preparing an alginate-agar bead inoculant from a Trichoderma seed culture;
   (b) cultivating the alginate-agar bead inoculant in liquid nutrient culture medium in a reactor to produce a desired scaled-up microbial density in the bead, wherein the desired scaled-up microbial density is at least $1 \times 10^9$ conidia per gram of the alginate-agar beads;
   (c) harvesting the alginate-agar bead inoculant from the liquid culture medium; and
   (d) preparing the liquid form Trichoderma-based product, wherein the cultivated alginate-agar bead inoculants are used to inoculate a submerged fermentation reactor, and preparing the solid-state Trichoderma-based product, wherein the cultivated alginate-agar bead inoculants are used to inoculate a solid-state fermentation reactor.

2. The method of claim 1, wherein the Trichoderma microorganism is selected from the group consisting of Trichoderma reesei, Trichoderma harzianum, Trichoderma viride, and Trichoderma hamatum.

3. The method of claim 1, wherein the step (a) comprises combining a 5% homogenous slurry of the seed culture with sterile nutrient medium, 1% agar and 2% sodium alginate to produce an inoculum solution; and using a dripping showering device to deposit drops of the inoculum solution into a mixing vessel containing 1% calcium chloride, wherein the drops form alginate-agar bead inoculants comprising nutrient components and particles of the microorganism embedded in alginate-agar mass.

4. The method of claim 1, wherein the step (b) comprises collecting the alginate-agar bead and then cultivating it in a reactor containing a sufficient volume of the liquid nutrient medium to permit a high concentration of *Trichoderma* mycelia to disperse inside and throughout the surface of the alginate-agar bead.

5. The method of claim 1, wherein the step (b) is performed for about 1 to about 10 days, under continuous aeration and agitation, at a temperature of about 28° C. to about 30° C. and pH of about 5.0 to about 6.5.

6. The method of claim 1, wherein after the step (c) but before the step (d), the method comprises processing the alginate-agar bead inoculant for storage, wherein processing comprises collecting the alginate-agar bead inoculant from the reactor and placing the bead into a cryopreservation solution comprising glycerol and water at a ratio of about 50%.

7. The method of claim 6, wherein the cryopreservation solution is in a container selected from the group consisting of a flask, tube, vial and dish.

8. The method of claim 7 wherein the container comprises up to 50 bead inoculants.

9. The method of claim 7, wherein the container is placed into a freezer at a temperature of −80° C. to −10° C.

10. The method of claim 7, wherein the container is placed into a refrigerator at a temperature of −10° C. to 4° C.

11. The method of claim 1, wherein in step (d) the preparing of the liquid form *Trichoderma*-based product comprises cultivating the inoculant in the reactor for about 1 to about 10 days, under continuous aeration and agitation, at a temperature of about 28° C. to about 30° C. and pH of about 5.0 to about 6.5, wherein the reactor has a working volume of at least 200 gallons.

12. The method of claim 11, wherein the concentration of *Trichoderma* is increased in the liquid culture of at least $1 \times 10^9$ propagules per milliliter, and optionally preservatives, additives, and/or pH adjusters are added.

13. The method of claim 1, wherein in step (d) the preparing of the solid-state *Trichoderma*-based product comprises mixing the harvested alginate-agar bead inoculants with a liquid nutrient medium and a solid or semi-solid substrate to form a mixture; spreading the mixture thinly onto heat proof trays; cultivating the mixture on the trays in an incubator at 30° C. for 3 to 10 days with constant aeration by ambient air.

14. The method of claim 13, wherein the incubator is a proofing oven.

15. The method of claim 13, wherein the substrate is vermiculite and the ratio of vermiculite to alginate-agar beads in the mixture is in the range of from 3:1 to 4:1.

16. The method of claim 13, wherein the substrate is foodstuff selected from the group consisting of corn flour, rice, beans and pasta.

17. The method of claim 13, further comprising increasing the temperature of the incubator to 40° C.; drying the trays for about 3 to about 4 days using dry air supplementation and vacuuming out moistened air to produce a dried product; grinding the dried product in a grinder to a desired particle size; and mixing the ground dried product with dry diatomaceous earth and commercial compost.

18. The method of claim 17, further comprising packaging the dried product mixed with diatomaceous earth and commercial compost in hermetically sealed bags for commercial use.

19. The method of claim 18, wherein the concentration of *Trichoderma* in the dried product after mixing with the diatomaceous earth and commercial compost is no less than $1 \times 10^6$ conidia per gram.

\* \* \* \* \*